United States Patent [19]

Treace et al.

[11] Patent Number: 4,510,627

[45] Date of Patent: Apr. 16, 1985

[54] OSSICULAR PROSTHESIS

[75] Inventors: Harry T. Treace, Hohenwald; Calvin Griggs, Memphis, both of Tenn.

[73] Assignee: Treace Medical, Inc., Memphis, Tenn.

[21] Appl. No.: 436,501

[22] Filed: Oct. 25, 1982

[51] Int. Cl.³ .............................................. A61F 1/00
[52] U.S. Cl. .............................................. 3/1; 3/1.9; 128/92 C
[58] Field of Search ........................ 3/1, 1.9; 128/92 D

[56] References Cited

U.S. PATENT DOCUMENTS

| | | | |
|---|---|---|---|
| 3,710,399 | 1/1973 | Hurst | 3/1.9 |
| 4,052,754 | 10/1977 | Homsy | 3/1.9 |
| 4,281,419 | 8/1981 | Treace | 3/1.9 |
| 4,287,616 | 9/1981 | Heimke et al. | 3/1.9 |
| 4,351,069 | 9/1982 | Ballintyn et al. | 3/1.9 |
| 4,392,562 | 7/1983 | Burton et al. | 3/1 |

FOREIGN PATENT DOCUMENTS 960010 10/1949 France .............................. 128/92 D Primary Examiner—Richard J. Apley
Assistant Examiner—David J. Isabella
Attorney, Agent, or Firm—Walker & McKenzie

[57] ABSTRACT

A prosthesis for replacing part or all of the ossicles of the ossicular chain in the tympanic cavity. The prosthesis includes a porous body having an enlarged head for being closely associated with the tympanic membrane and having an elongated shaft for being coupled to the fenestra vestibuli. A metal core is encased within the body for collecting sound vibrations from the tympanic membrane and for transmitting the collected sound vibrations to the fenestra vestibuli. The metal core has substantially higher sound vibration and collecting qualities than the porous body.

10 Claims, 10 Drawing Figures

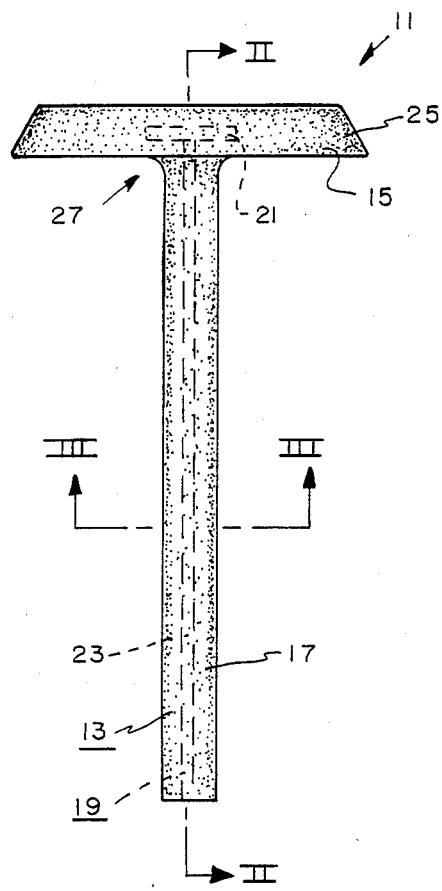
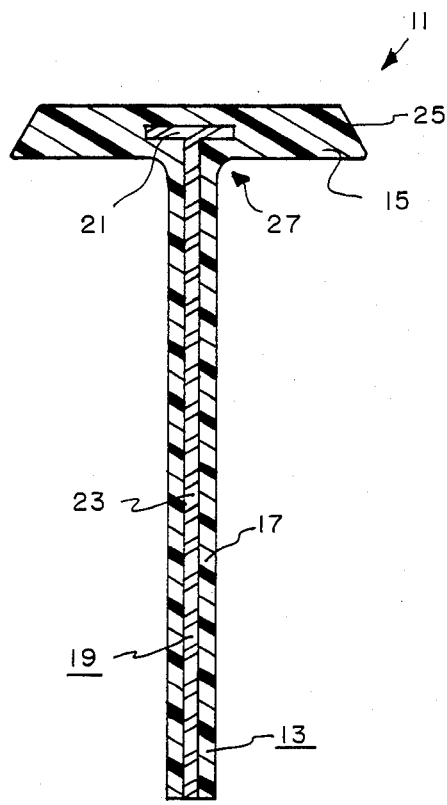
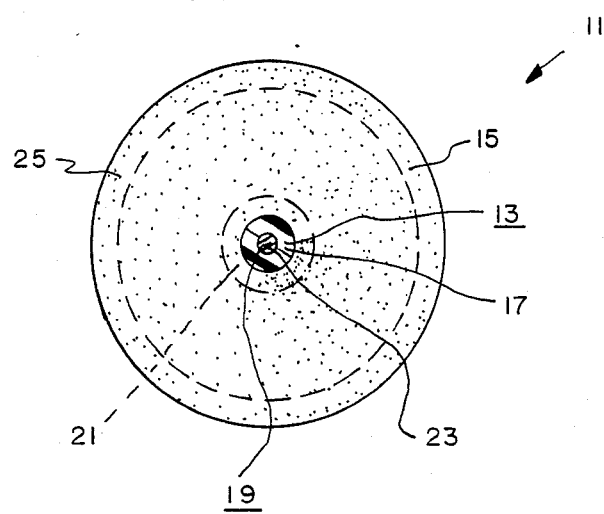

OSSICULAR PROSTHESIS

BACKGROUND OF THE INVENTION

1. Field of the Invention

The present invention relates to implants for replacing portions of or the entire ossicular chain in the tympanic cavity (i.e., the middle ear).

2. Description of the Prior Art

Various implants have heretofore been developed for replacing various parts of the ossicular chain in the middle ear. See, for example, Haase, U.S. Pat. No. 3,473,170 which discloses a middle ear prosthesis comprising a C-shaped arcuate frame member, a diaphragm extending across the front of the frame member for being placed in contact with the tympanic membrane, and a columella extending from the diaphragm at a point off-set from the center of the diaphragm for contacting the area of the oval window. A wire cord may extend inside the columella and out the distal end thereof to form a wire loop which can be looped through the footplate of the stapes. Mercandino, U.S. Pat. No. 3,191,188 discloses a hollow tubular strut which may extend between the tympanic membrane and a laminar base covering the oval window. Robinson, U.S. Pat. No. 3,196,462 discloses an elongated rod-like prosthesis to extend between the incus and oval window for replacing the stapes of the middle ear. Marquet, U.S. Pat. No. 3,566,413 discloses a prosthesis to connect the hammer to the stapes for replacing the anvil of the middle ear. Walchle, U.S. Pat. No. 3,722,003 discloses an L-shaped prosthesis for replacing the lenticular process of the stapes of the middle ear. Perkins, U.S. Pat. Nos. 4,014,976 and 4,077,069 disclose methods for making synthetic anatomical members such as a tympanic membrane and a malleus. None of the above patents disclose or suggest the present invention.

SUMMARY OF THE INVENTION

The present invention is directed toward improving ossicular prosthesis. The concept of the present invention is to provide a prosthesis of the type having an enlarged head for being closely associated with the tympanic membrane (i.e., the ear drum) and having an elongated shaft for being operatively coupled to the fenestra vestibuli (i.e., the oval window) to allow vibrations to be transmitted from the ear drum to the oval window with means for collecting sound vibrations from the ear drum and for transmitting the collected sound vibrations to the oval window, the core means having substantially higher sound vibration transmitting qualities than the body.

One object of the present invention is to provide an ossicular prosthesis which encourages tissue ingrowth while at the same time having good sound conductivity.

Another object of the present invention is to provide a strong ossicular prosthesis that can be permanently bent to conform with the angle of the ear drum and to accommodate any anomaly in the middle ear.

Another object of the present invention is to provide an ossicular prosthesis that can be easily cut and trimmed to proper shape and size.

Another object of the present invention is to provide an ossicular prosthesis that can be securely anchored to the stapes of the middle ear to prevent lateral displacement.

BRIEF DESCRIPTION OF THE DRAWINGS

FIG. 1 is a front elevational view of a first embodiment of the ossicular prosthesis of the present invention.

FIG. 2 is a sectional view as taken on line II—II of FIG. 1.

FIG. 3 is a sectional view as taken on line III—III of FIG. 1.

DESCRIPTION OF THE PREFERRED EMBODIMENTS

Figure 4:
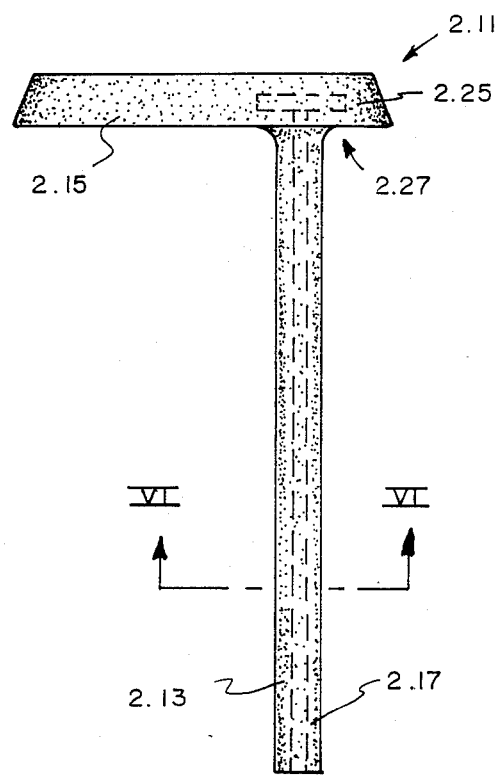
FIG. 4 is a front elevational view of a second embodiment of the ossicular prosthesis of the present invention.
Figure 5:
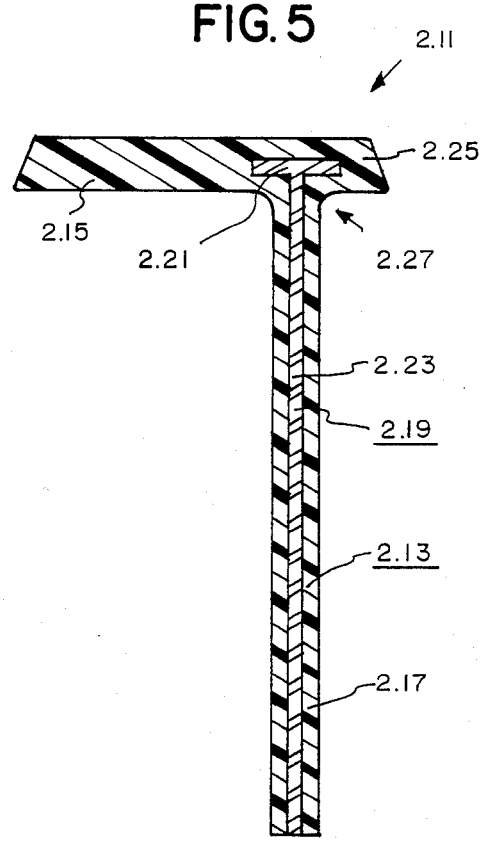
FIG. 5 is a sectional view of the prosthesis shown in FIG. 4.
Figure 6:
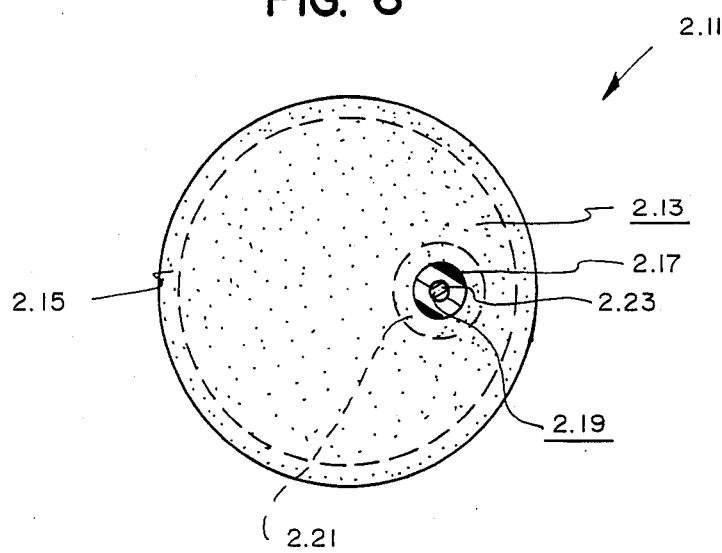
FIG. 6 is a sectional view as taken on line VI—VI of FIG. 4.

The tympanic cavity or middle ear (that part of the ear lying between the tympanic membrane or eardrum and the fenestra vestibuli or oval window) is bridged by three small bones or ossicles making up the ossicular chain that transmits sound vibrations from the eardrum to the oval window. The ossicular chain includes the malleus or hammer that is normally attached to the eardrum, the stapes or stirrup having a base or footplate fitting into the oval window, and the incus or anvil lying between the malleus and stapes. In certain disorders of the middle ear it becomes necessary for the otologist or ear surgeon to replace all or part of the ossicular chain. The present invention provides a prosthesis or implant for replacing all or part of the ossicles in the ossicular chain.

A first embodiment of the ossicular prosthesis of the present invention is shown in FIGS. 1-3, 7-9 and is identified by the numeral 11. The prosthesis 11 includes a body 13 having an enlarged head 15 for being closely associated with the eardrum and having an elongated shaft 17 for being operatively coupled to the oval window to allow vibrations to be transmitted from the eardrum to the oval window. The prosthesis 11 includes a core 19 encased within the body 13 for collecting sound vibrations from the eardrum and for transmitting the collected sound vibrations to the oval window. The core 19 has substantially higher sound vibration transmitting qualities than the body 13. The body 13 is preferably composed of a biocompatible porous meterial such as a porous ultrahigh molecular weight polyethylene which encourages tissue ingrowth. The core 19 is preferably composed of a biocompatible metallic material such as stainless steel which provides more than 5 times the sound conductivity of polyethylene.

The core 19 preferably includes an enlarged head 21 for being encased within the head 15 of the body 13, and preferably includes an elongated shaft 23 for being encased within the shaft 17 of the body 13. The head 21 and shaft 23 of the core 19 are preferably constructed as an integral, one-piece unit. Preferably, the head 21 and shaft 23 of the core 19 are machined out of a single piece of tissue tolerant and non-corrosive stainless steel. The head 15 and shaft 17 of the body 13 are preferably molded about the head 21 and shaft 23 of the core 19 out of porous ultrahigh molecular weight polyethylene to permanently bond the core 19 within the body 13.

The head 15 of the body 13 is permanently tiltable to any angle with respect to the longitudinal axis of the shaft 17 of the body 13. The head 15 of the body 13 preferably has a beveled edge 25 which will help to insure that the prosthesis 11 does not damage the tympanic membrane. The body 13 preferably includes a fillet portion 27 between the head 15 and the shaft 17 thereof for strengthening the section of the body 13 where it is most likely to be tilted.

A second embodiment of the present invention is shown in FIGS. 4, 5, 6 and 10 and is identified by the numeral 2.11. The prosthesis 2.11 is similar to the prosthesis 11 in construction including a body 2.13 having an enlarged head 2.15 and an elongated shaft 2.17, and including a core 2.19 having an enlarged head 2.21 encased within the head 2.15 of the body 2.13 and having an elongated shaft 2.23 encased within the shaft 2.17 of the body 2.13. The head 2.15 has a beveled edge 2.25. The body 2.13 includes a fillet 2.27 between the head 2.15 and shaft 2.17. The difference between the prosthesis 2.11 and the prosthesis 11 is that the head 2.15 of the body 2.13 is offset with respect to the shaft 2.17 of the body 2.13.

Figure 7:
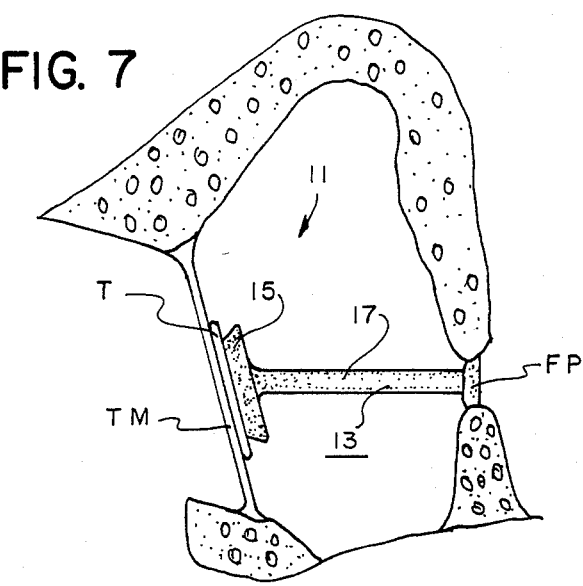
FIG. 7 is a somewhat diagrammatic sectional view of the middle ear showing the first embodiment of the ossicular prosthesis of the present invention implanted therein.
Figure 8:
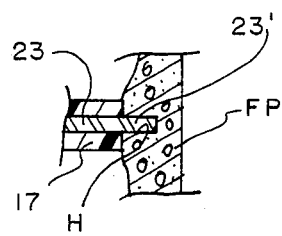
FIG. 8 is an enlarged sectional view of a portion of FIG. 7.
Figure 9:
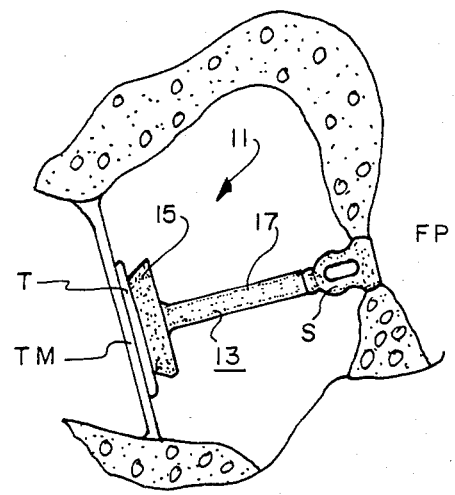
FIG. 9 is a view similar to FIG. 7 but with the entire stapes intact.
Figure 10:
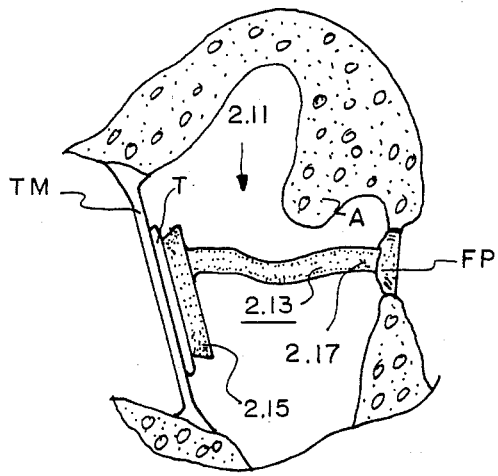
FIG. 10 is a view similar to FIG. 7 but showing the second embodiment of the ossicular prosthesis of the present invention implanted therein.

The method of using the ossicular prosthesis of the present invention will be apparent to those skilled in the art. FIG. 7 shows the prosthesis 11 implanted in the middle ear between the tympanic membrane TM and the footplate FP of a stapes in the case where the entire ossicular chain with the exception of the footplate FP of the stapes is replaced. A portion of tissue T is shown in FIG. 7 interfaced between the tympanic membrane TM and the face of the head 15 of the body 13. The tissue T may be a vein or other cartilage to thicken the tympanic membrane TM since the tympanic membrane in a diseased ear is usually thin. The tissue T allows quick adhesion of the prosthesis 11 to the tympanic membrane TM and also gives a cushioning efect to provide a good fit. FIG. 7 shows the head 15 of the body 13 permanently tilted with respect to the longitudinal axis of the shaft 17 thereof to correspond with the angle of the tympanic membrane TM. FIG. 8 discloses a manner in which the prosthesis 11 can be securely anchored to the footplate FP of the stapes to prevent lateral displacement thereof. That is, FIG. 8 discloses an extremely small hole H provided in the footplate FP and discloses a portion of the shaft 17 of the body 13 cut away from the shaft 23 of the core 19 to result in a pinlike distal end 23' on the shaft 23 that fits into the hole H to provide an anchoring means that discourages lateral displacement. The shaft 23 and hole H may have a diameter of about 0.127 millimeter. FIG. 9 is similar to FIG. 7 but discloses the prosthesis 11 being used with the entire stapes S of the ossicular chain. In such a case, a length of the distal end of the shaft 17 of the body 13 and shaft 23 of the core 19 is removed to provide a proper fit. When so used as a partial ossicular replacement, a hole may be formed in the head of the stapes for anchorage of the conducting shaft similar to that shown in FIG. 8. FIG. 10 is similar to FIGS. 7 and 9 but discloses the prosthesis 2.11 and shows a middle ear with an anomaly A in which the shaft 17 of the body 13 and shaft 23 of the core 19 must be permanently bent to ensure a proper fit of the prosthesis 2.11 within the middle ear.

The present invention provides a total or partial ossicular replacement implant or prosthesis that provides a sound collector platform (i.e., the head 21) which delivers sound through a sound conducting shaft (i.e., the shaft 23) directly to the point of anchorage at the oval window, that can be permanently bent to conform to the angle of the eardrum or the like and to thus allow the head 21 of the core 19 to be positioned substantially centrally of the eardrum (since sound vibrations are naturally collected at the center of the eardrum), that can be cut or be modified in size and shape by the surgeon to properly match the structure of the inner ear the prosthesis is being implanted in (e.g., the surgeon may, of course, cut the shafts 17, 23 to proper length and may also trim the head 15 to proper shape and size depending on the shape and dimensions of the specific inner ear which varies from patient to patient, etc.). The head 21 of the core 19 is preferably relatively small compared to the head 15 of the body 13 to cause the sound to be concentrated in the center of the prosthesis.

Although the present invention has been described and illustrated with respect to preferred embodiments thereof and preferred uses therefore, it is not to be so limited since changes and modifications can be made therein which are within the full intended scope of the invention.

We claim:

1. An ossicular replacement implant comprising:
   (a) a body including an elongated shaft having a first end forming an enlarged and substantially flat head portion, said head portion and said shaft being molded out of a biocompatible porous material as an integral one piece unit; and
   (b) a core encased within said body, said core having substantially higher sound transmitting qualities than said body, said core including an elongated core shaft aligned substantially concentric within said shaft of said body and further including a first end forming an enlarged and substantially flat head positioned within and substantially concentric within said head portion of said body; and wherein said body and said core being permanently bendable to allow said implant to be permanently bent to a specific shape by a surgeon during the implantation thereof to conform to the patient's middle ear structure, said core being stationary with respect to the body.

2. The implant of claim 1 in which said head and said shaft of said body and said head and said shaft of said core are substantially symmetrical with one another.

3. The implant of claim 1 in which said shaft of said body and said head and said shaft of said core are substantially symmetrical with one another, and in which said head of said body is offset with respect to said shaft of said body.

4. The prosthesis of claim 1 in which said body is composed of a biocompatible porous material and in which said core means is composed of a biocompatible metallic material.

5. The prosthesis of claim 4 in which said head and said shaft of said core means are constructed as an integral one-piece unit.

6. The prosthesis of claim 5 in which said head and said shaft of said core means are machined out of a single piece of stainless steel and in which said head and said shaft of said body are molded about said head and said shaft of said body out of porous ultra-high molecular weight polyethylene.

7. The prosthesis of claim 5 in which said head of said body is permanently tiltable to any angle with respect to the longitudinal axis of said shaft of said body.

8. The prosthesis of claim 7 in which said head of said body has a beveled edge.

9. The prosthesis of claim 8 in which said body includes a fillet portion between said head and shaft thereof for strengthening the section of said body where it is most likely to be tilted.

10. The prosthesis of claim 6 in which said shaft of said core means extends past said shaft of said body for allowing said shaft of said core means to be inserted into a portion of the ossicles to prevent lateral displacement of said prosthesis.

* * * * *

Notice of Adverse Decision in Interference

In Interference No. 101,534, involving Patent No. 4,510,627, H. T. Treace and C. Griggs, OSSICULAR PROSTHESIS, final judgment adverse to the patentees was rendered April 20, 1989, as to claims 1, 2, 4, 5, and 7.

[*Official Gazette September 19, 1989.*]